United States Patent [19]

Cherpeck

[11] Patent Number: 5,599,359
[45] Date of Patent: Feb. 4, 1997

[54] POLYALKYLPHENYL AND POLYALKYLOXYCARBONYLPHENYL HYDROXYBENZOATES AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 580,917

[22] Filed: Dec. 29, 1995

[51] Int. Cl.⁶ .................................................. C10L 1/18
[52] U.S. Cl. ........................... 44/388; 114/389; 114/403; 560/66; 560/72; 560/109
[58] Field of Search .................... 44/388, 389, 403; 560/66, 72, 109

[56]         References Cited

U.S. PATENT DOCUMENTS

| | | | |
|---|---|---|---|
| 3,285,855 | 11/1966 | Dexter et al. | 252/57 |
| 3,330,859 | 7/1967 | Dexter et al. | 260/473 |
| 3,849,085 | 11/1974 | Kreuz et al. | 44/78 |
| 4,049,713 | 9/1977 | Spivack | 260/559 R |
| 4,134,846 | 1/1979 | Machleder et al. | 252/51.5 A |
| 4,231,759 | 11/1980 | Udelhofen et al. | 44/75 |
| 4,320,021 | 3/1982 | Lange | 252/51.5 R |
| 4,347,148 | 8/1982 | Davis | 252/51.5 R |
| 4,713,475 | 12/1987 | Spivack et al. | 560/75 |
| 4,859,210 | 8/1989 | Franz et al. | 44/53 |
| 5,196,142 | 3/1993 | Mollet et al. | 252/311 |
| 5,196,565 | 3/1993 | Ross | 560/55 |
| 5,380,345 | 1/1995 | Cherpeck | 44/399 |
| 5,399,178 | 3/1995 | Cherpeck | 44/415 |

Primary Examiner—Prince Willis, Jr.
Assistant Examiner—Cephia D. Toomer
Attorney, Agent, or Firm—C. J. Caroli

[57]                 ABSTRACT

A compound of the formula:

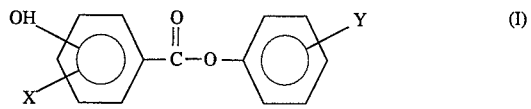

wherein X is hydrogen or hydroxy, and Y is —R or —C(O)O—R, wherein R is a polyalkyl group having an average molecular weight of about from 450 to 5000; or a fuel soluble salt thereof. The compounds of formula I are useful as hydrocarbon fuel additives for the prevention and control of deposits, especially intake valve deposits, in internal combustion engines.

33 Claims, No Drawings

POLYALKYLPHENYL AND POLYALKYLOXYCARBONYLPHENYL HYDROXYBENZOATES AND FUEL COMPOSITIONS CONTAINING THE SAME

BACKGROUND OF THE INVENTION

Field of the Invention

This invention relates to certain polyalkylphenyl and polyalkyloxycarbonylphenylhydroxy and dihydroxybenzoates. In a further aspect, this invention relates to the use of such compounds in fuel compositions to prevent and control engine deposits.

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

Nitro phenols have also been employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants and demulsifiers for lubricating oil and fuel compositions.

In addition, U.S. Pat. No. 4,231,759, issued Nov. 4, 1980 to Udelhofen et al., discloses a fuel additive composition comprising the Mannich condensation product of (1) a high molecular weight alkyl-substituted hydroxyaromatic compound wherein the alkyl group has a number average molecular weight of about 600 to about 3000, (2) an amine and (3) an aldehyde. This patent teaches that such Mannich condensation products provide carburetor cleanliness when employed alone, and intake valve cleanliness when employed in combination with a hydrocarbon carrier fluid.

U.S. Pat. No. 4,859,210, issued Aug. 22, 1989 to Franz et al., discloses fuel compositions containing (1) one or more polybutyl or polyisobutyl alcohols wherein the polybutyl or polyisobutyl group has a number average molecular weight of 324 to 3000, or (2) a poly(alkoxylate) of the polybutyl or polyisobutyl alcohol, or (3) a carboxylate ester of the polybutyl or polyisobutyl alcohol. This patent further teaches that when the fuel composition contains an ester of a polybutyl or polyisobutyl alcohol, the ester-forming acid group may be derived from saturated or unsaturated, aliphatic or aromatic, acyclic or cyclic mono- or polycarboxylic acids.

U.S. Pat. Nos. 3,285,855, and 3,330,859 issued Nov. 15, 1966 and Jul. 11, 1967 respectively, to Dexter et al., disclose alkyl esters of dialkyl hydroxybenzoic and hydroxyphenylalkanoic acids wherein the ester moiety contains from 6 to 30 carbon atoms. These patents teach that such esters are useful for stabilizing polypropylene and other organic material normally subject to oxidative deterioration. Similar alkyl esters containing hindered dialkyl hydroxyphenyl groups are disclosed in U.S. Pat. No. 5,196,565, which issued Mar. 23, 1993 to Ross and trialkylhydroxyaromatic carboxylic acids, amides and esters are disclosed in U.S. Pat. No. 4,049,713 which issued Sep. 20, 1977 to Spivack. Also, 4'-hydroxyphenyl propanoate esters are disclosed in U.S. Pat. No. 4,713,475 which issued to Spivack Dec. 15, 1987.

U.S. Pat. No. 5,196,142, issued Mar. 23, 1993 to Mollet et al., discloses alkyl esters of hydroxyphenyl carboxylic acids wherein the ester moiety may contain up to 23 carbon atoms. This patent teaches that such compounds are useful as antioxidants for stabilizing emulsion-polymerized polymers.

My prior co-pending commonly assigned U.S. application Ser. No. 08/144,980, filed Oct. 28, 1993, (International Application PCT/U.S.94/12365, Publication No. WO 95/11955, published May 4, 1995) hereby incorporated by reference in its entirety discloses certain polyalkyl hydroxyaromatic esters which provide control of engine deposits, including intake valve deposits, when employed as fuel additives in fuel compositions. My prior U.S. Pat. No. 5,399,178 discloses certain Mannich condensation products of the compounds disclosed in said U.S. application Ser. No. 08/144,980 and my U.S. Pat. No. 5,380,345 discloses certain polyalkyl amino and nitroaromatic esters useful as fuel additives to control engine deposits, both of which patents are hereby incorporated by reference in their entireties.

SUMMARY OF THE INVENTION

It has now been discovered that certain polyalkylphenyl hydroxybenzoates and polyalkyloxycarbonylphenyl hydroxybenzoates provide excellent control of engine deposits, particularly intake valve deposit control, when employed as fuel additives in fuel compositions.

More specifically the compounds of the present invention can be represented by the following formula:

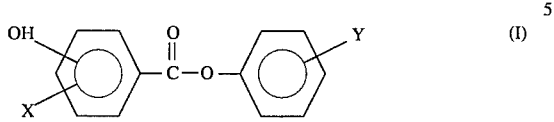 (I)

wherein X is hydrogen or hydroxy, and Y is —R or —C(O)OR wherein R is a polyalkyl group having an average molecular weight in the range of about from 450 to 5000.

In general, the commercial product will be a mixture of compounds according to formula I because the polyalkyl benzoic acid starting materials are generally a mixture because the commercial sources of polyalkylene are generally mixtures. In general, there is no commercial reason to isolate individual compounds. If desired the individual compounds of formula I could be prepared by using individual compounds as starting material and by isolating individual compounds from the product. But, as noted above, there is in general no commercial reason to isolate particular compounds when the product is used as a fuel additive and it would be uneconomical to do so.

The present invention further provides a fuel composition comprising a major amount of hydrocarbons boiling in the gasoline or diesel range and an amount of a compound or mixture of compounds of the present invention which is effective to control engine deposits.

The present invention additionally provides a fuel concentrate comprising an inert stable oleophilic organic solvent boiling in the range of from about 150° F. to 400° F. and from about 10 to 70 weight percent of a compound or mixture of compounds of the present invention.

The invention further provides a method of controlling engine deposits especially intake valve deposits, via the use of fuels containing a deposit controlling effective amount of a compound or mixture of compounds of the present invention.

The invention further provides a method for preparing the aforedescribed compositions.

FURTHER DESCRIPTION OF THE INVENTION AND PREFERRED EMBODIMENTS

Preferably, R is a polyalkyl group having an average molecular weight in the range of about 700 to 5000, more preferably about 700 to 3000, and most preferably about 900 to 2500.

It is also preferred that where the hydroxybenzoate moiety contains only one hydroxy group, i.e., where X is hydrogen, the hydroxy group is situated para to the carbonyloxy group linking the two phenyl rings. Similarly, it is also preferred that the Y substituent on the other phenyl ring is located para to the carbonyloxy linking group. Where the hydroxybenzoate moiety contains two hydroxy groups, i.e., X is hydroxy, it is preferred that the two hydroxy substituents are located in the para and meta positions relative to the carbonyloxy linking group.

In general compounds used for fuel additives will have a sufficient molecular weight so as to be non-volatile at normal engine intake valve operating temperatures (about 200°–250° C.). Preferably, the compound and salts of the present invention will have a molecular weight of about from 900 to 3500. The primary considerations in selecting a particular polyalkyl substituent are volatility and fuel solubility of the results compound and not the technical molecular weight of the product mixture. However, overall best performance is generally obtained wherein the polyalkyl substituent has an average molecular weight of about from 700 to 3000.

Fuel soluble salts of the compounds formula I are also useful for preventing or controlling engine deposits and in some cases may improve solubility. Suitable salts include, for example, those obtained by deprotonation of the hydroxy substituent with a base. Such salts include, for example, salts of alkali metals, alkaline earth metals, ammonia, and substituted ammonium salts. The primary criteria for selecting a salt is fuel solubility. Preferred salts are derived from alkali metals, alkaline earth metals and substituted ammonium salts, for example, tetraalkyl ammonium salts, such as tetrabutyl ammonium.

Definitions

As used herein, the following terms have the following meanings unless expressly stated to the contrary.

The term "polyalkyl" refers to alkyl groups which are generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The term "fuel" refers to liquid hydrocarbon compounds such as petroleum fuels or synthetic fuels which are useful as fuels in spark ignition or combustion fire engines and may also contain minor amounts of other auxiliary fuels.

The term "engine" refers to internal combustion engines and includes both spark ignition engines and combustion fired engines such as diesel engines.

Synthesis

The compounds of formula I can be prepared by esterification of the appropriately substituted benzoic acid with the appropriately substituted phenol:

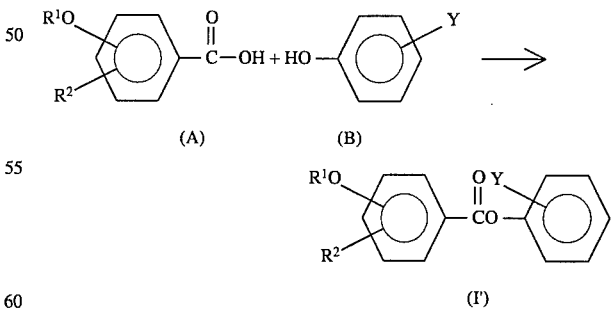

wherein Y is as defined herein above; is hydrogen or $R^2$ —$OR^3$, and $R^1$ and $R^3$ are independently hydrogen or, preferably, a suitable hydroxy protecting group, for example, benzyl, t-butyldimethylsilyl, etc. Deprotection of the aromatic hydroxy group(s) on the esters of Formula I' provides the compounds of Formula I.

The above process can be conveniently conducted by contacting compound (A) with compound (B) under reactive conditions in the presence of an acidic catalyst. The reaction can be conducted neat or optionally may be conducted in an inert solvent or organic liquid reaction medium. Typically, the reaction is conducted at temperatures in the range of about from 70° C. to 160° C., for about from 0.5 to 48 hours, using mole ratios of reactants in the range of about from 0.25 to 1.5 molar equivalents of a benzoic acid of Formula (A) per mole of a phenol of Formula (B). Suitable acid catalysts which can be used include, for example, p-toluene sulfonic acid, methanesulfonic acid and the like. Typical inert organic solvents or liquid diluents (liquid reaction medium) which can be used include, for example, benzene, toluene, xylene, and the like and compatible mixtures thereof. Water generated by this reaction is preferably removed during the course of the reaction, for example, by azeotropic distillation.

The unprotected compounds of formula A are hydroxybenzoic acids or dihydroxybenzoic acids and are generally known compounds and can be prepared by known procedures. Similarly, the compounds of formula B wherein Y is polyalkyl are polyalkylphenols and also are generally known compounds and can be prepared by known alkylation procedures or obvious modification. Such procedures are, for example, described in U.S. Pat. No. 4,744,921. The compounds of formula B wherein Y is —C(O)O-polyalkyl can be prepared by the procedures described in my International application Ser. No. PCT/U.S.94/12365 published May 4, 1995 as WO 95/11955 and also in my U.S. Pat. No. 5,399,178, both of which are hereby incorporated by reference in their entirety. In accordance with the procedures described therein, compounds of Formula B wherein Y is —C(O)O— polyalkyl can be prepared by esterifying a hydroxybenzoic acid having the formula:

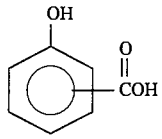 (D)

with a polyalkyl alcohol having the formula:

HO—R (E)

wherein R is as defined above, using conventional esterification reaction conditions.

The benzoic compounds of formula D are hydroxybenzoic acids and as noted above are known compounds and can be prepared from known compounds by conventional procedures. Suitable hydroxybenzoic acids for use as starting materials in this procedure include 3-hydroxybenzoic acid, 4-hydroxybenzoic acid, and 3,4-dihydroxybenzoic acid. Preferred hydroxybenzoic acids are 4-hydroxybenzoic acid and 3,4-dihydroxybenzoic acid.

The polyalkyl alcohols of formula E may also be prepared by conventional procedures known in the art. Such procedures are taught, for example, in U.S. Pat. No. 5,055,607 to Buckley and U.S. Pat. No. 4,859,210 to Franz et al., the disclosures of which are incorporated herein by reference in their entirety.

In general, the polyalkyl alcohols of formula E will be selected so that the resulting polyalkyl substituent on the compounds of the present invention will have the number average molecular weight indicated above; i.e., substitutent R of formula E will correspond to substituent R of formula I.

The polyalkyl substituent on the polyalkyl alcohols and polyalkyl phenols employed in this invention may be generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The preferred polyisobutenes used to prepare the presently employed polyalkyl alcohols and polyalkyl phenols are polyisobutenes which comprise at least about 20% of the more reactive methylvinylidene isomer, preferably at least 50% and more preferably at least 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808. Such polyisobutenes, known as "reactive" polyisobutenes, yield high molecular weight alcohols in which the hydroxyl group is at or near the end of the hydrocarbon chain.

Examples of suitable polyisobutenes having a high alkylvinylidene content include Ultravis 30, a polyisobutene having a molecular weight of about 1300 and a methylvinylidene content of about 74%, and Ultravis 10, a polyisobutene having a molecular weight of about 950 and a methylvinylidene content of about 76%, both available from British Petroleum.

The polyalkyl alcohols may be prepared from the corresponding olefins by conventional procedures. Such procedures include hydration of the double bond to give an alcohol. Suitable procedures for preparing such long-chain alcohols are described in I. T. Harrison and S. Harrison, *Compendium of Organic Synthetic Methods,* Wiley-Interscience, N.Y. (1971), pp. 119–122, as well as in U.S. Pat. Nos. 5,055,607 and 4,859,210.

Likewise, the polyalkylphenols of Formula B wherein Y is polyalkyl may be prepared from the corresponding olefins by conventional procedures. For example, the polyalkylphenols of Formula B above may be prepared by reacting the appropriate olefin or olefin mixture with phenol in the presence of an alkylating catalyst at a temperature of from about 60° C. to 200° C., and preferably 125° C. to 180° C. either neat or in an essentially inert solvent at atmosphere pressure. A preferred alkylating catalyst is a sulfonic acid catalyst such as Amberlyst 15 ® available from Rohm and Haas, Philadelphia, Pa. Molar ratio of reactants may be used. Alternatively, molar excess of phenol can be employed, i.e., 2–2.5 equivalents of phenol for each equivalent of olefin with unreacted phenol recycled. The latter process maximizes monoalkylphenol. Examples of inert solvents include benzene, toluene, chlorobenzene and 250 thinner which is a mixture of aromatics, paraffins and naphthenes.

The esterification of the hydroxybenzoic acid of Formula D with a polyalkyl alcohol of Formula E to produce the polyalkyl hydroxybenzoate compounds of formula B can be conducted in an analogous manner as the esterification described above with respect to the preparation of the compounds of formula I. Typically, the reaction will be conducted by contacting a polyalkyl alcohol of formula E with about 0.25 to about 1.5 molar equivalents of a hydroxyaromatic carboxylic acid of formula D in the presence of an acidic catalyst at a temperature in the range of about 70° C. to about 160° C. for about 0.5 to about 48 hours. Suitable acid catalysts for this reaction include p-toluene sulfonic acid, methanesulfonic acid and the like. The reaction may be conducted in the presence or absence of an inert solvent, such as benzene, toluene and the like. The water generated by this reaction is preferably removed during the course of the reaction by, for example, azeotropic distillation with an inert solvent, such as toluene.

The compounds of formula I can also be conveniently synthesized by reacting the compounds of formula B with an acyl halide of formula A'.

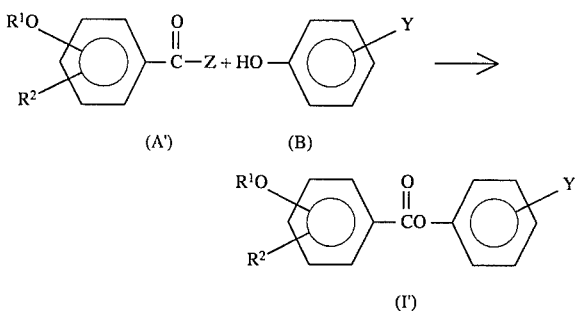

wherein $R^1$, $R^2$ and Y are as defined hereinabove and Z is halide preferably chloride or bromide.

Typically, this reaction is conducted by contacting an alcohol of formula B with about 0.9 to about 1.5 molar equivalents of an acyl halide of formula A' in an inert solvent, such as toluene, dichloromethane, diethyl ether, and the like, at a temperature in the range of about 25° C. to about 150° C. The reaction is generally complete in about 0.5 to about 48 hours. Preferably, the reaction is conducted in the presence of a sufficient amount of a scavenger base neutralizing the acid generated during the reaction. Typical scavenger bases include amines such as, for example, triethylamine, di(isopropyl)ethylamine, pyridine or 4-dimethylaminopyridine. Also in most cases the free hydroxy substituents on the starting material will be protected with a suitable protecting group, e.g., benzyl, etc. In general the acyl halide is prepared from the corresponding hydroxybenzoic acid and the hydroxy group will be protected prior to formation of the acyl halide. Correspondingly, in most cases the hydroxy group will be protected in the products of formula I'.

Deprotection of the aromatic hydroxyl group(s) on the esters of formula I' then provides a polyalkyl phenyl or polyalkyloxycarbonylphenyl hydroxybenzoic acid ester of formula I. Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction is conducted in an inert solvent, preferably a mixture of ethyl acetate and acetic acid, at a temperature of from about 0° C. to about 40° C. for about 1 to about 24 hours.

Acyl halides of formula A' are also generally known compounds and, in any event can be prepared from the corresponding hydroxy or dihydroxybenzoic acids of formula A in which the hydroxy group are preferably protected with a suitable protection group:

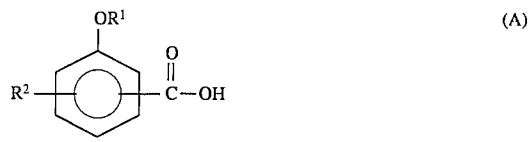

wherein $OR^1$ is a protected hydroxy group and $R^2$ is hydrogen or a protected hydroxy group as defined above, and then converting the carboxylic acid moiety of formula A into an acyl halide using conventional procedures.

Protection of the aromatic hydroxyl groups of formula A may be accomplished using well known procedures. The choice of a suitable protecting group for a particular hydroxyaromatic carboxylic acid will be apparent to those skilled in the art. Various protecting groups, and their introduction and removal, are described, for example, in T. W. Greene and P. G. M. Wuts, *Protective Groups in Organic Synthesis,* Second Edition, Wiley, N.Y., 1991, and references cited therein. Alternatively, the protected derivatives of formula A can be prepared from known starting materials other than the corresponding hydroxyaromatic compounds by conventional procedures.

The carboxylic acid moiety of formula A may be converted into an acyl halide by contacting a compound according to formula A with an inorganic acid halide, such as thionyl chloride, phosphorous trichloride, phosphorous tribromide, or phosphorous pentachloride; or alternatively, with oxalyl chloride. Generally, this reaction will be conducted using about 1 to 5 molar equivalents of the inorganic acid halide or oxalyl chloride, either neat or in an inert solvent, such as diethyl ether, at a temperature in the range of about 20° C. to about 80° C. for about 1 to about 48 hours. A catalyst, such as N,N-dimethylformamide, may also be used in this reaction.

General Process Conditions

It should be appreciated that where typical or preferred process conditions (e.g., reaction temperatures, times, mole ratios of reactions, solvents, pressures, etc.) are given, other process conditions may also be used unless otherwise stated. Optimum reaction conditions may vary with the particular reactants or solvents used, but such conditions can be determined by one skilled in the art by routine optimization procedures.

Moreover, those skilled in the art will recognize that it may be necessary to block or protect certain functional groups while conducting the above synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis,* Second Edition, Wiley, N.Y., 1991, and references cited therein.

In the above synthetic procedures, a hydroxyl group will preferably be protected, when necessary, as the benzyl or tert-butyldimethylsilyl ether. Introduction and removal of these protecting groups is well described in the art.

The products or product mixtures can be recovered from the respective reaction product mixtures by any suitable separation and purification procedure, such as, for example, extraction, evaporation, and recrystallization. Suitable separation and purification procedures for recovering product mixtures are, for example, illustrated in the Examples.

Fuel Compositions

The compounds of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the compounds of this invention in hydrocarbon fuel will range from about 50 to about 2500 parts per million (ppm) by weight, preferably from 75 to 1000 ppm. When other deposit control additives are present, a lesser amount of the present additive may be used.

The compounds of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 wt. %, preferably 10 to 50 wt. %, more preferably from 20 to 40 wt. %.

In gasoline fuels, other fuel additives may be employed with the additives of the present invention, including, for example, oxygenates, such as t-butyl methyl ether, anti-knock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present. The gasoline fuels may also contain amounts of other fuels such as, for example, methanol.

In diesel fuels, other well-known additives can be employed, such as pour point depressants, flow improvers, cetane improvers, and the like. The diesel fuels can also include other fuels such as, for example, methanol. A fuel-soluble, nonvolatile carrier fluid or oil may also be used with the compounds of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis, and polyesters, such as those described, for example, in U.S. Pat. Nos. 3,756,793 and 5,004,478 to Robinson and Vogel et al., respectively, and in European Patent Application Nos. 356,726 and 382,159, published Mar. 7, 1990 and Aug. 16, 1990, respectively.

These carrier fluids are believed to act as a carrier for the fuel additives of the present invention and to assist in removing and retarding deposits. The carrier fluid may also exhibit synergistic deposit control properties when used in combination with a compound of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1. When employed in a fuel concentrate, carrier fluids will generally be present in amounts ranging from about 20 to about 60 wt. %, preferably from 30 to 50 wt. %.

PREPARATIONS AND EXAMPLES

A further understanding of the invention can be had in the following nonlimiting Examples. Herein, unless expressly stated to the contrary, all temperatures and temperature ranges refer to the Centigrade system and the term "ambient" or "room temperature" refers to about 20° C.–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 300 mHz, signals are assigned as singlets (s), broad singlets (bs), doublets (d), double doublets (dd), triplets (t), double triplets (dr), quartets (q), and multiplets (m), and cps refers to cycles per second.

EXAMPLES

Example 1

Preparation of Polyisobutyl Phenol

To a flask equipped with a magnetic stirrer, reflux condenser, thermometer, addition funnel and nitrogen inlet was added 203.2 grams of phenol. The phenol was warmed to 40° C. and the heat source was removed. Then, 73.5 milliliters of boron trifluoride etherate was added dropwise. 1040 grams of Ultravis 10 polyisobutene (molecular weight 950, 76% methylvinylidene, available from British Petroleum) was dissolved in 1,863 milliliters of hexane. The polyisobutene was added to the reaction at a rate to maintain the temperature between 22°–27° C. The reaction mixture was stirred for 16 hours at room temperature. Then, 400 milliliters of concentrated ammonium hydroxide was added followed by 2,000 milliliters of hexane. The reaction mixture was washed with water (3×2,000 milliliters), dried over magnesium sulfate, filtered and the solvents removed under vacuum to yield 1,056.5 grams of a crude reaction product. The crude reaction product was determined to contain 80% of the desired product by proton NMR and chromatography on silica gel eluting with hexane, followed by hexane: ethylacetate: ethanol (93:5:2).

Example 2

Preparation of 4-Benzyloxybenzoyl Chloride

To a flask equipped with a magnetic stirrer and drying tube was added 75.0 grams of 4-benzyloxybenzoic acid and 700 mL of anhydrous methylene chloride and then 72 mL of oxalyl chloride. The resulting mixture was stirred at room temperature for 16 hours and then the solvent was removed in vacuo to yield 79.6 grams of the desired acid chloride.

Example 3

Preparation of

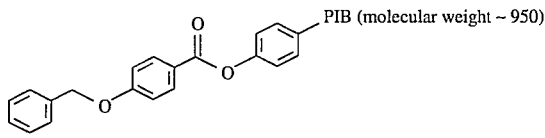

4-Benzyloxybenzoyl chloride (6.0 grams, prepared as in Example 2), polyisobutyl phenol (25.0 grams, chromatographed material prepared as in Example 1), triethylamine (3.5 mL), 4-dimethylaminopyridine (1.5 grams) and anhydrous toluene (300 mL) were combined. The resulting mixture was refluxed under nitrogen for 16 hours. The reaction was diluted with 600 mL of diethyl ether and was washed twice with saturated aqueous sodium bicarbonate solution and once with brine. The organic layer was dried over anhydrous magnesium sulfate, filtered and the solvents removed in vacuo to yield 35.3 grams as a yellow oil. The oil was chromatographed on silica gel, eluting with hexane/ethyl acetate (95:5) to yield 29.0 grams of the desired product as a light yellow oil.

Example 4

Preparation of

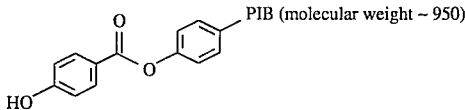

A solution of 29.0 grams of the product from Example 3 in 100 mL of ethyl acetate and 100 mL of acetic acid containing 3.0 grams of 10% palladium on charcoal was hydrogenolyzed at 35–40 psi for 16 hours on a Parr low-pressure hydrogenator. Catalyst filtration and removal of the residual acetic acid with toluene in vacuo yielded 21.7 grams of the desired product as an oil. $^1$H NMR (CDCl$_3$,D$_2$O) δ8.1 (d, 2H), 7.4 (d, 2H), 7.1 (d, 2H), 6.9 (d, 2H), 0.7–1.8 (m, 137H).

Example 5

Preparation of Polyisobutyl 4-Hydroxybenzoate

To a flask equipped with a mechanical stirrer, thermometer, Dean Stark trap, reflux condensor and nitrogen inlet was added 525 grams of polyisobutanol (average molecular weight 984, prepared via hydroformylation of polyisobutene sold under the trademark Amoco H-100), 124.7 grams of 4-hydroxybenzoic acid, and 13.0 grams of p-toluenesulfonic acid. The mixture was stirred at 130° C. for 16 hours, cooled to room temperature and diluted with 2 liters of diethyl ether. The organic phase was washed two times with saturated aqueous sodium bicarbonate, once with brine, dried over anhydrous magnesium sulfate, filtered and concentrated in vacuo to yield 514.3 grams of the desired product as a yellow oil IR (neat) 1715 1685 cm$^{-1}$; $^1$H NMR (CDCl$_3$) L 7.95 (d, 2H), 6.9 (d, 2H), 5.8 (bs, 1H), 4.3 (t, 2H), 0.6–1.8 (m, 137H).

Similarly, by applying the above-described procedure using the appropriate average molecular weight polyalkyl alcohol and substituted hydroxybenzoic acid, the following compounds can be prepared:

Polypropyl (Mn 450) 4-Hydroxybenzoate

Polyisobutyl (Mn 2100) 3-hydroxybenzoate

Polydecyl (Mn 3500) 4-Hydroxybenzoate

Polyoctyl (Mn 4500) 4-Hydroxybenzoate

Example 6

Preparation of

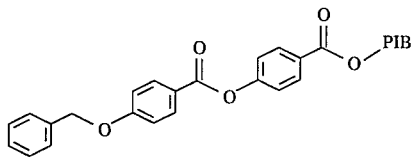

4-Benzyloxybenzoyl chloride (5.7 grams, prepared as in Example 2), the phenol prepared as in Example 5 (26.2 grams), triethylamine (3.4 mL), 4-dimethylaminopyridine (1.4 grams) and anhydrous toluene (400 mL) were combined. The resulting mixture was refluxed under nitrogen for 16 hours. The reaction was diluted with 800 mL of diethyl ether and was washed twice with saturated aqueous sodium bicarbonate solution and once with brine. The organic layer was dried over anhydrous magnesium sulfate, filtered and the solvents removed in vacuo to yield 20.0 grams as a light yellow oil. The oil was chromatographed on silica gel, eluting with hexane/ethyl acetate (95:5) to yield 14.0 grams of the desired product as a light yellow oil.

Example 7

Preparation of

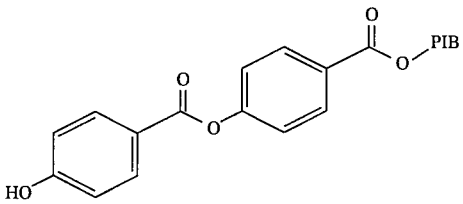

A solution of 14.0 grams of the product from Example 3 in 100 mL of ethyl acetate and 100 mL of acetic acid containing 2.0 grams of 10% palladium on charcoal was hydrogenolyzed at 35–40 psi for 16 hours on a Parr low-pressure hydrogenator. Catalyst filtration and removal of the residual acetic acid with toluene in vacuo yielded 9.7 grams of the desired product as an oil. $^1$H NMR (CDCl$_3$,D$_2$O) δ8.1 (d, 4H), 7.35 (d, 2H), 6.95 (d, 2H), 4.3 (t, 2H), 0.7–1.8 (m, 137H).

Example 8

Preparation of

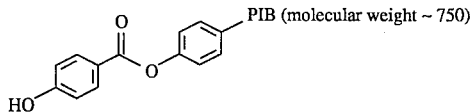

The procedures of Examples 1–4 were repeated using BP Hyvis 5 polyisobutene (molecular weight 750, available from British Petroleum) in Example 1 instead of Ultravis 10 polyisobutene. The resulting product had the following NMR Spectrum: $^1$H NMR (CDCl$_3$,D$_2$O) δ8.1 (d, 2H), 7.1–7.4 (m, 4H), 6.9 (d, 2H), 0.7–1.8 (m, 105H).

Example 9

Single-Cylinder Engine Test

The test compounds identified in Tables I and II hereinbelow were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 400 BTC; engine speed is 1800 rpm; the crankcase oil is a commercial 30W oil.

The amount of carbonaceous deposit in milligrams on the intake valves is reported for each of the test compounds in Table I and Table II.

TABLE I

| Sample[1] | Intake Valve Deposit Weight (in milligrams) | | |
|---|---|---|---|
| | Run 1 | Run 2 | Average |
| Base Fuel | 169.1 | 157.3 | 163.2 |
| Example 4 | 52.0 | 80.3 | 66.2 |
| Example 8 | 59.0 | 40.3 | 49.7 |

[1] At 150 parts per million actives (ppma).

TABLE II

| Sample[1] | Intake Valve Deposit Weight (in milligrams) | | |
|---|---|---|---|
| | Run 1 | Run 2 | Average |
| Base Fuel | 294.8 | 297.5 | 296.2 |
| Example 7 | 76.0 | 80.0 | 78.0 |

[1] At 150 parts per million actives (ppma).

The base fuel employed in the above single-cylinder engine tests was a regular octane unleaded gasoline containing no fuel detergent. The test compounds were admixed with the base fuel to give a concentration of 150 ppma (parts per million actives).

The data in Table I and Table II illustrates the significant reduction in intake valve deposits provided by the polyalkylphenyl and polyalkyloxycarbonylphenyl hydroxybenzoates of the present invention (Examples 4, 7 and 8) compared to the base fuel.

Obviously, many modifications and variations of the invention described hereinabove and below can be made without departing from the essence and scope thereof.

What is claimed is:

1. A compound having the formula:

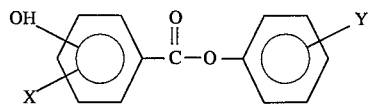

wherein X is hydrogen or hydroxy, and Y is —R or —C(O)O—R, wherein R is a polyalkyl group having an average molecular weight of about from 450 to 5000; or a fuel soluble salt thereof.

2. The compound according to claim 1, wherein X is hydrogen.

3. The compound according to claim 1, wherein R is a polyalkyl group having an average molecular weight of about from 700 to 5000.

4. The compound according to claim 3, wherein R is a polyalkyl group having an average molecular weight of about from 700 to 3000.

5. The compound according to claim 4, wherein R is a polyalkyl group having an average molecular weight of about from 900 to 2500.

6. The compound according to claim 2, wherein the hydroxy substituent is at the para position of the phenyl ring to which it is attached, relative to the carbonyloxy substituent.

7. The compound according to claim 1, wherein the Y substituent is located at the para position of the phenyl ring to which it is attached, relative to the carbonyloxy substituent.

8. The compound according to claim 1, wherein Y is a polyalkyl group, R.

9. The compound according to claim 1, wherein Y is —C(O)O—R.

10. The compound according to claim 1, wherein X is hydroxy.

11. The compound according to claim 10, wherein one of the hydroxy groups is at the para position and the other is at the meta position of the phenyl ring to which they are attached, relative to the carbonyloxy substituent.

12. A fuel composition comprising a major amount of hydrocarbons boiling in the gasoline or diesel range and an amount effective to control engine deposits of a compound having the formula:

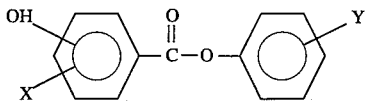

wherein X is hydrogen or hydroxy, and Y is —R or —C(O)O—R, wherein R is a polyalkyl group having an average molecular weight of about from 450 to 5000; or a fuel soluble salt thereof.

13. The fuel composition according to claim 12, wherein X is hydrogen.

14. The fuel composition according to claim 12, wherein R is a polyalkyl group having an average molecular weight of about from 700 to 5000.

15. The fuel composition according to claim 14, wherein R is a polyalkyl group having an average molecular weight of about from 700 to 3000.

16. The fuel composition according to claim 15, wherein R is a polyalkyl group having an average molecular weight of about from 900 to 2500.

17. The fuel composition according to claim 13, wherein the hydroxy substituent is at the para position of the phenyl ring to which it is attached, relative to the carbonyloxy substituent.

18. The fuel composition according to claim 12, wherein the Y substituent is located at the para position of the phenyl ring to which it is attached, relative to the carbonyloxy substituent.

19. The fuel composition according to claim 12, wherein Y is a polyalkyl group, R.

20. The fuel composition according to claim 12, wherein Y is —C(O)O—R.

21. The fuel composition according to claim 12, wherein X is hydroxy.

22. The fuel composition according to claim 21, wherein one of the hydroxy groups is at the para position and the other is at the meta position of the phenyl ring to which they are attached, relative to the carbonyloxy substituent.

23. A fuel concentrate comprising an inert stable oleophilic organic solvent boiling in the range of about from 150° F. to 400° F. and about from 10 to 70 weight percent of a compound having the formula:

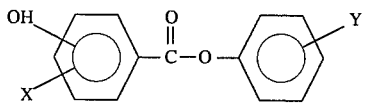

wherein X is hydrogen or hydroxy, and Y is —R or —C(O)O—R, wherein R is a polyalkyl group having an average molecular weight of about from 450 to 5000; or a fuel soluble salt thereof.

24. The fuel concentrate according to claim 23, wherein X is hydrogen.

25. The fuel concentrate according to claim 23, wherein R is a polyalkyl group having an average molecular weight of about from 700 to 5000.

26. The fuel concentrate according to claim 25, wherein R is a polyalkyl group having an average molecular weight of about from 700 to 3000.

27. The fuel concentrate according to claim 26, wherein R is a polyalkyl group having an average molecular weight of about from 900 to 2500.

28. The fuel concentrate according to claim 24, wherein the hydroxy substituent is at the para position of the phenyl ring to which it is attached, relative to the carbonyloxy substituent.

29. The fuel concentrate according to claim 23, wherein the Y substituent is located at the para position of the phenyl ring to which it is attached, relative to the carbonyloxy substituent.

30. The fuel concentrate according to claim 23, wherein Y is a polyalkyl group, R.

31. The fuel concentrate according to claim 23, wherein Y is —C(O)O—R.

32. The fuel concentrate according to claim 23, wherein X is hydroxy.

33. The fuel concentrate according to claim 32, wherein one of the hydroxy groups is at the para position and the other is at the meta position of the phenyl ring to which they are attached, relative to the carbonyloxy substituent.

* * * * *